United States Patent
Krause et al.

(10) Patent No.: US 6,254,850 B1
(45) Date of Patent: Jul. 3, 2001

(54) METAL COMPLEXES, SUITABLE FOR USE IN DIAGNOSIS AND THERAPY

(75) Inventors: Werner Krause; Franz-Karl Maier; Michael Bauer; Gabriele Schuhmann-Giampieri; Wolf-Rudiger Press, all of Berlin; Peter Muschik, Ladeburg, all of (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/480,153

(22) Filed: Jan. 10, 2000

Related U.S. Application Data

(63) Continuation of application No. 08/488,287, filed on Jul. 7, 1995, now Pat. No. 6,040,432.

(30) Foreign Application Priority Data

Feb. 21, 1995  (DE) ............................................. 195 07 820

(51) Int. Cl.[7] ......................... A61K 51/04; C07F 13/00; C07F 5/00; C07F 229/00; A61B 5/055
(52) U.S. Cl. ............... 424/1.65; 424/9.364; 424/9.365; 534/16; 562/443; 562/446; 562/564; 562/556; 562/565; 556/45; 556/57; 556/138; 556/148
(58) Field of Search ................... 534/16, 10, 14; 424/1.65, 9.36, 9.364, 9.365; 562/443, 446, 564, 556, 565; 556/45, 57, 138, 148; 564/368; 560/38, 39, 169

(56) References Cited

U.S. PATENT DOCUMENTS

| | | | |
|---|---|---|---|
| 4,622,420 | 11/1986 | Meares et al. | 562/443 |
| 4,647,447 | 3/1987 | Gries et al. | 424/9 |
| 4,808,541 | 2/1989 | Mikola et al. | 436/501 |
| 5,077,037 | 12/1991 | Wallace | 424/9 |
| 5,141,740 | 8/1992 | Rajagopalan et al. | 424/9 |
| 5,182,370 | 1/1993 | Felder et al. | 534/16 |
| 5,198,208 | 3/1993 | Berg et al. | 424/1.1 |
| 5,250,285 | 10/1993 | Lauffer et al. | 424/9 |
| 5,395,608 | 3/1995 | Troutner et al. | 424/1.49 |
| 5,482,699 | 1/1996 | Amen et al. | 424/9.42 |
| 5,514,810 | 5/1996 | Platzek et al. | 548/300.1 |

FOREIGN PATENT DOCUMENTS

| | | |
|---|---|---|
| 0 230 893 | 8/1987 | (EP) . |
| 0 367 223 | 5/1990 | (EP) . |
| 0 405 704 | 1/1991 | (EP) . |
| 0 450 742 | 10/1991 | (EP) . |
| 0 071 564 | 2/1993 | (EP) . |

OTHER PUBLICATIONS

Fossheim et al., J. Med. Chem., vol. 34, 1991, pp. 819–826.

Williams et al., J. Org. Chem., vol. 58, 1993, pp. 1151–1158.

G. Vittadini E. Felder, et al., "B–19036, A Potential New Hepatobiliary Contrast Agent for MR Proton Imaging", *Invest. Radiology*, 23 (Suppl. 1):S246–248, 1988.

*Primary Examiner*—Michael G. Hartley
(74) *Attorney, Agent, or Firm*—Millen, White, Zelano & Branigan, P.C.

(57) ABSTRACT

The invention relates to diethylenetriaminepentaacetic acid derivatives, their complexes and complex salts, containing an element of atomic numbers 20–32, 39–51 or 57–83, pharmaceutical agents containing these compounds, their use as contrast media and antidotes and process for their production.

18 Claims, No Drawings

METAL COMPLEXES, SUITABLE FOR USE IN DIAGNOSIS AND THERAPY

This application is a continuation of application Ser. No. 08/488,287 filed on Jun. 7, 1995, now U.S. Pat. No. 6,040,432.

The invention relates to the objects characterized in the claims, i.e., DTPA derivatives substituted in a novel way, their metal complexes, pharmaceutical agents containing these complexes, their use in diagnosis and therapy as well as process for the production of complexes and agents.

Contrast media are indispensable additives in modern diagnosis; thus many diseases could not be diagnosed without the use of contrast media. Contrast media are used in all areas of diagnosis, such as, e.g., diagnostic radiology, radiodiagnosis or ultrasound diagnosis or magnetic resonance tomography.

The selection of the method preferred in each case depends, i.a., on the diagnostic problem, but is also determined by the choice of apparatus available in each case to the physician. Thus, because of the considerable technical expenditure and associated high cost, in particular nuclear spin tomography has not yet found the wide use of other methods, such as, e.g., methods of diagnostic radiology.

The selection of the suitable contrast medium also varies on the basis of the respective problem. Thus, the suitability of the contrast medium for a specific object is determined last but not least by its concentration and distribution behavior in the organism.

Although great progress has been achieved both on the equipment side and on the contrast medium side, solutions satisfactory for all problems are not yet available.

Thus, suitable contrast media do not exist for all indications for the various imaging processes. In particular, until now, no suitable x-ray contrast medium for liver diagnosis has been available.

In diagnostic radiology, basically contrast media based on triiodobenzene have been able to gain acceptance, since these compounds exhibit a high x-ray opacity, a low general and local toxicity and are very readily water-soluble.

Such compounds are described, e.g., in EP 0 105 752, EP 0 015 867. But the latter show insufficient concentration in the liver for an imaging.

The radio-opaque effect of an x-ray contrast medium is basically dependent on the size of the mass attenuation coefficient of the elements, contained in the compound, in the diagnostic range of radiation. In addition to iodine-containing compounds, complexes of metals of higher atomic numbers are also suitable as x-ray contrast media. Physiologically compatible complex compounds of these metals are already widely used in the field of NMR diagnosis. In general, these are metal complexes, as they are described, e.g., in EP 0 071 564.

Wo 93/16375 describes metal complexes, which are linked by amide bonds to iodine-substituted aromatic compounds. These compounds are to allow both NMR and x-ray investigations to be performed with only one administration of contrast medium. A combination of the two imaging processes is advantageous in many cases for a differentiated visualization and a reliable determination of certain diseases. These compounds are to be suitable especially for angiography. As the reprocessing of the production samples revealed, however, the compounds show insufficient concentration in the area of the liver for x-ray investigations.

Liver-specific NMR contrast media are described in EP 0 405 704. These should also be suitable in principle for diagnostic radiology because of the metal content in the complexes. A reprocessing of the experimental samples showed insufficient contrasting of the liver in the x-ray picture in the animal experiment itself with administration of a high dose (conc.: 1 mol/l, dose: 0.5 mmol of Gd/kg intravenously). A sufficient imaging effect in diagnostic radiology is only achieved with a dose in which the safety margin is reduced to a measurement that is no longer justifiable.

The object of this invention was therefore to make available very well-tolerated and water-soluble contrast media, as well as a process for their production that is as simple as possible, which are suitable for NMR diagnosis, diagnostic radiology and radiodiagnosis or radiotherapy—especially for diagnostic radiology of the liver.

This object is achieved by the substances, agents, production processes and uses characterized in the claims. It has been found that metal complexes of general formula I

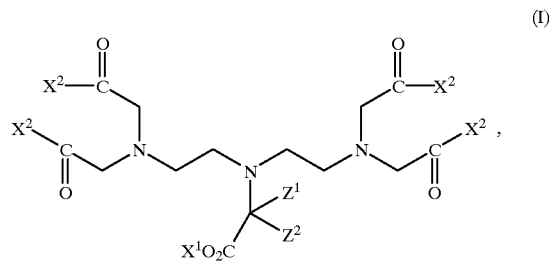

in which $X^1$ independently of one another, stand for a hydrogen atom or a metal ion equivalent of an element of atomic numbers 20–32, 39–51 or 57–83, $X^2$ independently of one another, stand for a group $O-X^1$ with $X^1$ in the above-indicated meaning or $N(R')R^2$ in which $R^1$, $R^2$ independently of one another, stand for a hydrogen atom or for a saturated or unsaturated, branched or straight-chain $C_1-C_{20}$ chain, in which the chain or parts of the chain can form a cyclic or bicyclic unit, which is interrupted by zero to three oxygen and/or sulfur atoms and/or zero to three sulfoxyl and/or sulfono groups and is substituted by zero to six phenyl, pyridyl, $R^3S$, $R^3OOC$ and/or $R^3O$ groups, which further contains zero to three

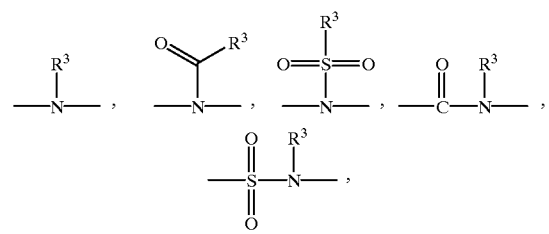

carbonyl and/or thiocarbonyl groups, and optionally present aromatic groups can be substituted one to three times, independently of one another, by $R^3O_2C$,

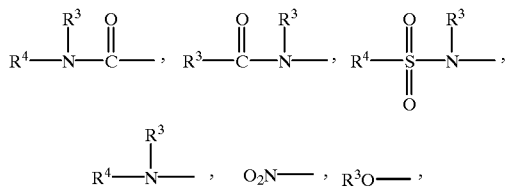

and/or $R^4$ groups or $R^1$ and $R^2$ together, with inclusion of the common amide nitrogen atom, form a four- to eight-membered ring, which can contain two additional oxygen atoms and/or two carbonyl groups in which at least two of the radicals referred to with $X^1$ stand for a metal ion equivalent of the above-mentioned metals, $Z^1$ stands for a saturated or unsaturated, branched or straight-chain $C_1$–$C_{20}$ chain, in which the chain or parts of the chain can form a cyclic or bicyclic unit, which is interrupted by zero to three oxygen and/or sulfur atoms and/or zero to three sulfoxy and/or sulfono groups and is substituted by zero to six phenyl, pyridyl, $R^3S$, $R^3OOC$ and/or $R^3O$ groups, which further contains zero to three

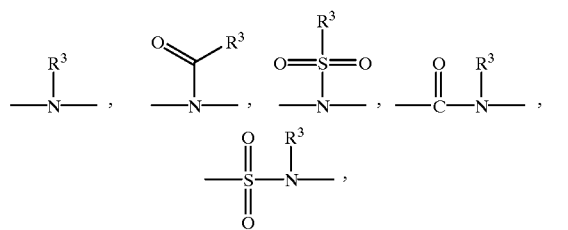

carbonyl and/or thiocarbonyl groups, and optionally present aromatic groups can be substituted singly or repeatedly, independently of one another, by $R^3O_2C$

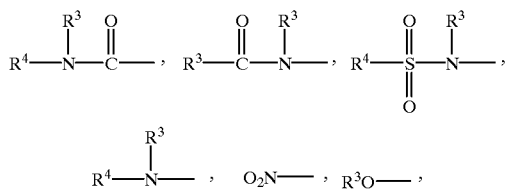

and/or $R^4$ groups, $Z^2$ stands for a hydrogen atom or for a saturated or unsaturated, branched or straight-chain $C_1$–$C_{20}$ chain, in which the chain or parts of the chain can form a cyclic or bicyclic unit, which is interrupted by zero to three oxygen and/or sulfur atoms and/or zero to three sulfoxy and/or sulfono groups, and is substituted by zero to six phenyl, pyridyl, $R^3S$, $R^3OOC$ and/or $R^3O$ groups, which further contains zero to three

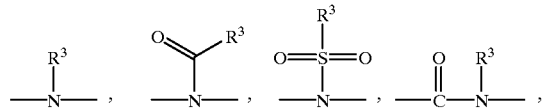

-continued

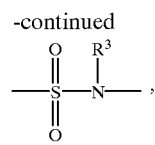

carbonyl and/or thiocarbonyl groups, and optionally present aromatic groups can be substituted one to three times, independently of one another, by $R^3O_2C$,

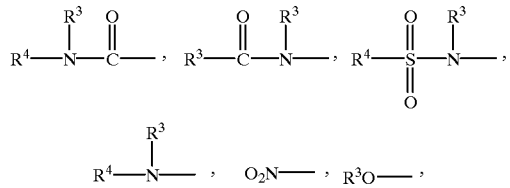

and/or $R^3$ groups, $R^3$ independently of one another, stand for a hydrogen atom, a phenyl radical or a straight-chain, branched or cyclic $C_1$–$C_6$ radical, which is interrupted by zero to two oxygen atoms and/or zero to two phenylene groups and is substituted with zero to three HO, HOOC radical and/or zero to two phenyl radicals, $R^4$ independently of one another, stand for a phenyl radical or a straight-chain, branched or cyclic $C_1$–$C_6$ radical, which is interrupted by zero to two oxygen atoms and/or zero to two phenylene groups and is substituted with zero to three HO, HOOC radicals and/or zero to two phenyl radicals, and if $Z^2$ stands for a hydrogen atom, radical $Z^1$ does not stand for an unsubstituted $C_6$–$C_{10}$ aryl radical or $Z^1$ and $Z^2$ together with inclusion of the common α-carbon atom form a three- to eight-membered ring or a bicyclic compound with seven to 15 carbon atoms, in which free carboxylic acid groups, not used for complexing, of the compounds of general formula I according to the invention can also be present in the form of their salts with physiologically compatible inorganic and/or organic cations, are excellently suited for the production of contrast media for diagnostic radiology and/or NMR diagnosis, preferably of contrast media for diagnostic radiology, especially for diagnostic radiology of the liver, the bile ducts and the gallbladder.

The invention therefore relates to the compounds of general formula I.

Compounds of general formula I in which all occurring radicals $X^1$ have the meaning of hydrogen atoms have been referred to as complexing agents. Compounds of general formula I in which at least two of the radicals referred to with $X^1$ have the meaning of a metal ion equivalent are referred to as complexes.

If the metal complex according to the invention is intended for the production of agents for diagnostic radiology, the central ion must be derived from an element of a higher atomic number to achieve a sufficient absorption of the x rays. It has been found that elements of atomic numbers 57–83 are suitable for this purpose. Especially suitable are complexes of the elements lanthanum, gadolinium, terbium, dysprosium, holmium, erbium, ytterbium, lutetium, bismuth and hafnium.

If the metal complex according to the invention is intended for the production of agents for NMR diagnosis, the central ion must be paramagnetic. It has been found that for this purpose, especially the chromium(III), iron(II), cobalt(II), nickel(II), copper(II), praseodymium(III), neodymium(III), samarium(III) and the ytterbium(III) ions are suitable. Especially preferred are complexes of the ions gadolinium(III), terbium(III), dysprosium(III), holmium (III), erbium(III), iron(III) and manganese(II).

If the metal complex according to the invention is intended for the production of agents for nuclear medicine, the central ion must be radioactive. Suitable are, for example, the radioisotopes of the elements copper, cobalt, gallium, germanium, yttrium, strontium, technetium, indium, ytterbium, gadolinium, samarium, silver, gold, rhenium, bismuth and iridium.

The compounds according to the invention can contain, as groups of formula —C(=O)X$^2$, carboxylates (—CO$_2$X$^1$) or carboxylic acid amides (—C(=O)N(R$^1$)R$^2$). As radicals R$^1$ and R$^2$, there can be mentioned, for example, hydrogen atoms, straight-chain and branched C$_1$–C$_{20}$ alkyl radicals optionally interrupted by 1–3 oxygen atoms and/or substituted by 1–3 carboxy groups, as well as phenyl and benzyl radicals.

Preferred radicals R$^1$ and R$^2$ are hydrogen atoms, methyl, benzyl and/or C$_1$–C$_{11}$ carboxyalkyl radicals.

Radicals R$^1$ and R$^2$ can also form, together with inclusion of the amide nitrogen atom, whose substituents they are, a four- to eight-membered ring, which can contain zero to two additional oxygen atoms and/or zero to two additional carbonyl or sulfonyl groups. If R$^1$ and R$^2$ together stand for a ring system, the morpholine ring or the S, S-dioxothiomorpholine ring is preferred.

As group Z$^1$, there can be mentioned as examples straight-chain or branched, saturated or unsaturated C$_1$–C$_{20}$ chains, which can be interrupted by 0 to three oxygen, sulfur and/or nitrogen atoms. The chain can also exhibit cyclic or bicyclic units, such as phenyl, phenylene, naphthyl, naphthylene, adamantyl radicals. It can carry up to six hydroxy, alkoxy, carboxy, carboxyalkyl, phenyl or pyridyl substituents. Should the chain exhibit aromatic groups, the latter, on their part, can carry hydroxy, alkoxy, carboxy, carboxyalkyl, nitro, amino, acylamino and/or carbamide substituents.

As preferred radicals Z$^1$, there can be mentioned: hexyl, heptyl, octyl, nonyl, decyl, undecyl, dodecyl, tridecyl, tetradecyl, pentadecyl, hexadecyl, heptadecyl, octadecyl, nonadecyl, icosyl, cyclopentyl, cyclohexyl, cycloheptyl, cyclooctyl, cyclopentanone, cyclohexanol, 2-hydroxyethyl, 5-oxononyl, 2-ethylhexyl, 2-ethoxyhexyl, phenyl, benzyl, naphthyl, imidazolyl and/or thiazolyl radicals as well as radicals of formulas CH$_2$OH, CH$_2$CH$_2$OH, CH$_2$OCH$_3$, CH$_2$OC$_6$H$_5$, CH$_2$OC$_6$H$_4$—CH$_3$, CH$_2$C$_6$H$_4$—NO$_2$, CH$_2$C$_6$H$_4$—CH$_3$, CH$_2$OC$_6$H$_4$—OCH$_3$, CH$_2$OC$_6$H$_4$—OC$_2$H$_5$, CH$_2$C$_6$H$_4$—OC$_2$H$_5$, CH$_2$C$_6$H$_4$—OCH$_2$C$_6$H$_5$, CH$_2$C$_6$H$_4$CH$_2$C$_6$H$_5$, CH$_2$C$_6$H$_4$C$_4$H$_9$, CH$_2$C$_6$H$_4$—OC$_3$H$_7$, CH$_2$C$_6$H$_4$C$_3$H$_7$, CH$_2$C$_6$H$_4$—OC$_4$H$_9$, (CH$_2$)$_{1-2}$—OCH$_2$C$_6$H$_5$, (CH$_2$)$_{1-2}$—S—CH$_2$C$_6$H$_5$, (CH$_2$)$_{1-2}$—OCH$_2$C$_6$H$_4$CH$_3$, (CH$_2$)$_{1-2}$—S—CH$_2$C$_6$H$_4$CH$_3$, (CH$_2$)$_{1-2}$CH$_2$C$_6$H$_4$C$_2$H$_5$, (CH$_2$)$_{1-2}$S—CH$_2$C$_6$H$_4$C$_2$H$_5$, (CH$_2$)$_{1-2}$CH$_2$C$_6$H$_4$C$_3$H$_7$, (CH$_2$)$_{1-2}$S—CH$_2$C$_6$H$_4$C$_3$H$_7$, (CH$_2$)$_{1-2}$OCH$_2$C6H$_4$C$_4$H$_9$, (CH$_2$)$_{1-2}$S—CH$_2$C$_6$H$_4$C$_4$H$_9$, (CH$_2$)$_{1-2}$CH$_2$C$_6$H$_4$C$_6$H$_5$, (CH$_2$)$_{1-2}$S—CH$_2$C$_6$H$_4$C$_6$H$_5$, (CH$_2$)$_{1-2}$—OCH$_2$C$_6$H$_4$—OCH$_3$, (CH$_2$)$_{1-2}$—S—CH$_2$C$_6$H$_4$—OCH$_3$, (CH$_2$)$_{1-2}$OCH$_2$C$_6$H$_4$—OC$_2$H$_5$, (CH$_2$)$_{1-2}$S—CH$_2$C$_6$H$_4$—OC$_2$H$_5$, (CH$_2$)$_{1-2}$CH$_2$C$_6$H$_4$—OC$_3$H$_7$, (CH$_2$)$_{1-2}$S—CH$_2$C$_6$H$_4$—OC$_3$H$_7$, (CH$_2$)$_{1-2}$OCH$_2$C$_6$H$_4$—OC$_4$H$_9$, (CH$_2$)$_{1-2}$S—CH$_2$C$_6$H$_4$—OC$_4$H$_9$, (CH$_2$)$_{1-2}$OCH$_2$C$_6$H$_4$—OC$_6$H$_5$, (CH$_2$)$_{1-2}$S —CH$_2$C$_6$H$_4$OC6H$_5$, CO$_2$H, CH$_2$CO$_2$H, (CH$_2$)$_{1-19}$CO$_2$H, (CH$_2$)$_4$NHC(O)C$_6$H$_5$ (CH$_2$)$_4$NHC(O)CH$_2$CH$_2$CO$_2$H. and Further, especially preferred groups Z$^1$ are radicals of formulas

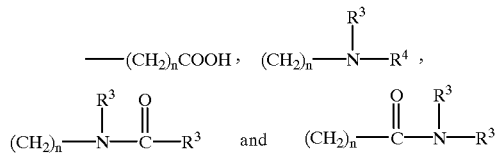

and, in which n stands for numbers 1 to 19 and R$^3$, independently of one another, stand for a hydrogen atom, a phenyl radical or a straight-chain, branched or cyclic C$_1$–C$_6$ radical, which is interrupted by zero to two oxygen atoms and/or zero to two phenylene groups and is substituted with zero to three HO, HOOC radicals and/or zero to two phenyl radicals.

R$^4$, independently of one another, stand for a phenyl radical or a straight-chain, branched or cyclic C$_1$–C$_6$ radical, which is interrupted by zero to two oxygen atoms and/or zero to two phenylene groups and is substituted with zero to three HO, HOOC radicals and/or zero to two phenyl radicals.

Also especially preferred groups Z$^1$ are radicals of formula —(CH$_2$)$_p$(C$_6$H$_4$)—C$_q$H$_{(2q+1)}$, in which p and q stand for numbers 1 to five, and the sum of p+q is greater than 4.

Especially preferred groups Z$^1$ are further radicals of formulas

—(CH$_2$)$_m$(C$_6$H$_4$)—R$^5$, in which R$^5$ stands for a butyl, phenyl or benzyl radical, and m stands for numbers 1 to 4, —(CH$_2$)$_m$(C$_6$H$_4$)—O—R$^6$, in which R$^6$ stands for a hydrogen atom, a C$_1$–C$_6$ alkyl radical or a phenyl or benzyl radical, and m stands for numbers 1 to 4, as well as —CH$_2$(C$_6$H$_4$)—O—R$^7$, in which R$^7$ stands for a methyl, ethyl, n-propyl, isopropyl, n-butyl, isobutyl, tert-butyl, phenyl or benzyl radical.

Quite especially preferred groups Z$^1$ are further radicals of formulas —CH$_2$—C$_6$H$_4$—C$_4$H$_9$, —CH$_2$—C$_6$H$_4$—OC$_4$H$_9$, —CH$_2$—C$_6$H$_4$—CH$_2$C$_6$H$_5$ and —CH$_2$—C$_6$H$_4$—O—CH$_2$C$_6$H$_5$.

As group Z$^2$, the radicals mentioned as Z$^1$ are suitable. In addition, Z$^2$ can stand for a hydrogen atom or for a methyl, ethyl, propyl, butyl or pentyl radical.

Z$^2$ preferably stands for a hydrogen atom, if Z$^1$ stands for radicals —CH$_2$—C$_6$H$_4$—C$_4$H$_9$, —CH$_2$—C$_6$H$_4$—OC$_4$H$_9$, —CH$_2$—C$_6$H$_4$—CH$_2$C$_6$H$_5$ or —CH$_2$—C$_6$H$_4$—O—CH$_2$C$_6$H$_5$.

Z$^2$ does not stand for a hydrogen atom, if Z$^1$ stands for an unsubstituted C$_6$–C$_{10}$ aryl radical.

Groups Z$^1$ and Z$^2$ can also, together with inclusion of the carbon atom, whose substituents they are, form a ring or a bicyclic compound. As examples, there are shown:

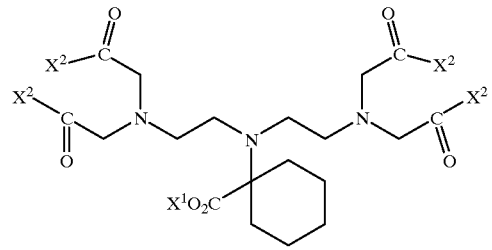

-continued

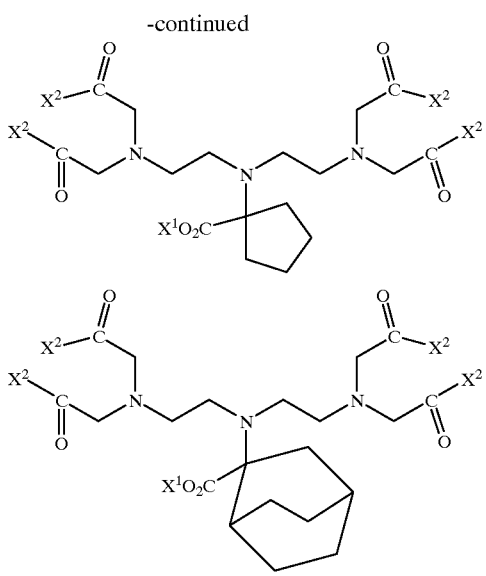

As physiologically compatible cations, there can be mentioned as examples sodium$^+$, calcium$^{2+}$, magnesium$^{2+}$ and zinc$^{2+}$ as well as organic cations such as meglumine, glucosamine, arginine, ornithine, lysine and ethanolamine.

Production of the Complexes According to the Invention

The production of the complexes according to the invention takes place in the way in which it was disclosed in patent specifications EP 71564, EP 130934 and DE-OS 3401052, by the metal oxide or a metal salt (for example, a chloride, nitrate, acetate, carbonate or sulfate) of the element of atomic numbers 20–32, 39–51 or 57–83 being dissolved or suspended in water and/or another polar solvent (such as methanol, ethanol, isopropanol or N,N-dimethylformamide) and being reacted with the solution or suspension of the equivalent amount of the complexing agent of general formula Ib

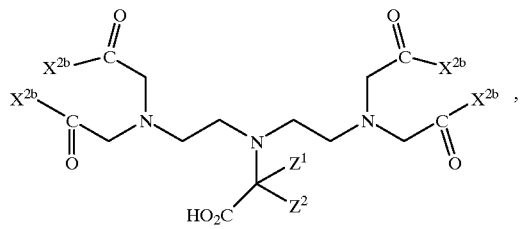
(Ib)

in which $Z^1$ and $Z^2$ have the above-mentioned meanings, $X^{2b}$ independently of one another, stand for a group HO or $N(R^1)R^2$ with $R^1$, $R^2$ in the above-mentioned meaning, and then, if desired, existing acid hydrogen atoms of acid groups being substituted by cations of inorganic and/or organic bases or amino acids.

In this case, the neutralization takes place with the help of inorganic bases (e.g., hydroxides, carbonates or bicarbonates) of, e.g., sodium, potassium or lithium and/or organic bases, such as, i.a., primary, secondary and tertiary amines, such as, e.g., ethanolamine, glucamine, N-methyl and N,N-dimethylglucamine, as well as basic amino acids, such as, e.g., lysine, arginine and ornithine.

For the production of neutral complex compounds, enough of the desired bases can be added, for example, to the acid complex salts in aqueous solution or suspension so that the neutral point is reached. The obtained solution can then be evaporated to dryness in a vacuum. Often, it is advantageous to precipitate the formed neutral salts by the addition of water-miscible solvents, such as, e.g., lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired base as early as during the complexing of the reaction mixture and thus to save a process step.

If the acid complexes contain several free acid groups, it is often suitable to produce neutral mixed salts, which contain both inorganic and organic cations as counterions.

This can happen, for example, by the complexing agents being reacted in aqueous suspension or solution with the oxide or salt of the desired element and half of the amount of an organic base required for neutralization, the formed complex salt being isolated, optionally purified and then mixed with the required amount of inorganic base for complete neutralization. The sequence of the addition of base can also be reversed.

Another possibility to arrive at neutral complex compounds consists in converting the remaining acid groups, as described, e.g., in EP 0450742, completely or partially to amides.

If the agents according to the invention are to contain radioisotopes, the production of the complexes from the complexing agents can take place according to the methods described in "Radiotracers for Medical Applications," Vol. I, CRC Press, Boca Raton, Fla.

Production of the Complexing Agents According to the Invention

The production of the compounds of general formula I takes place, for example, in that first an amino acid derivative of general formula II

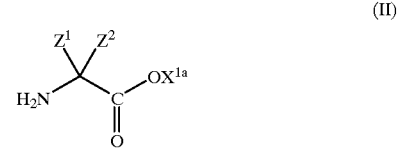
(II)

in which $Z^1$ and $Z^2$ have the above-indicated meaning and $X^{1a}$ stands for a straight-chain or branched $C_1$–$C_4$ alkyl group or an optionally substituted benzyl group, preferably a tert-butyl or a benzyl group, is reacted with two alkylation structural elements of general formula III

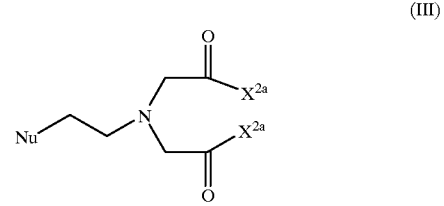
(III)

in which

Nu stands for a nucleofuge, such as, e.g., a chloride, bromide, iodide, O-mesylate, O-tosylate or O-triflate and $X^{2a}$ in each case independently of one another, stands for a group $X^{1a}$-O with $X^{1a}$ in the meaning mentioned in formula II or $N(R^1)R^2$ with $R^1$ and $R^2$ in the above-mentioned meaning.

Preferred amino acid derivatives are the esters of α-amino acids that are commercially available or known in the literature. Especially preferred are the esters of α-amino acids which contain a longer alkyl chain (>$C_4$) and/or an aromatic radical. Quite especially preferred are esters of 3-phenylalanine derivatives, whose phenyl radical is substituted in 4-position with an alkyl or alkoxy radical.

The reaction of compound II with compound III takes place preferably in a buffered alkylation reaction, in which an aqueous phosphate buffer solution is used as buffer. The reaction takes place at pHs 7–11, but preferably at pH 8. The buffer concentration can be between 0.1–2.5 M, but a 2 M phosphate-buffer solution preferably is used. The temperature of the alkylation can be between 0 and 50° C., the preferred temperature is room temperature.

The reaction is performed in a polar solvent, such as, e.g., acetonitrile, tetrahydrofuran, 1,4-dioxane or 1,2-dimethoxyethane. Acetonitrile is preferably used.

But the alkylation of the amine of formula II with compounds of formula III can also take place in a polar, aprotic solvent with use of an auxiliary base (such as, e.g., triethylamine).

The α-amino acid esters of general formula II, used in the reaction, can be produced from the commercially available amino acids according to methods known to one skilled in the art (e.g., Houben-Weyl, Methoden der organischen Chemie [Methods of Organic Chemistry], Synthese von Peptiden (Synthesis of Peptides), Part II, Volume XV/2, Georg Thieme Verlag Stuttgart, 1974, p. 3 ff). As commercially available products, α-amino acids and derivatives can be obtained, e.g., with the Fluka Chemie [Fluka Chemistry] AG, CH-9470 Buchs or the BACHEM Feinchemikalien [BACHEM Fine Chemicals] AG, CH-4416 Bubendorf.

Preferred amino acid derivatives of general formula II are amino acid benzyl, amino acid-tert-butyl, amino acid isopropyl and amino acid ethyl esters. In the synthesis of these compounds, salts (such as, e.g., hydrochlorides, hydrosulfates, sulfates, phosphates or p-toluenesulfonates) generally accumulate, which can be used directly in the reaction.

The structural element of general formula III used in the alkylation can be produced analogously to the description of Rapoport (J. Org. Chem., 58, 1151 (1993)) if $X^2$ stands for the tert-butoxy group and Nu stands for a bromine atom. If one or both groups $X^2$ should have the meaning of an amide, the production can be established analogously to the way mentioned in Example 4 or according to other processes familiar to one skilled in the art.

After the N,N-dialkylation of the respective α-amino acid ester (e.g., of the tyrosine benzyl ester), further reactions on its functional groups can take place (in this case, e.g., an 0-alkylation of the obtained tyrosine derivative).

The complexing agents of general formula Ib are produced by cleavage of acid protective groups $X^{1a}$ from the obtained compounds of general formula Ia

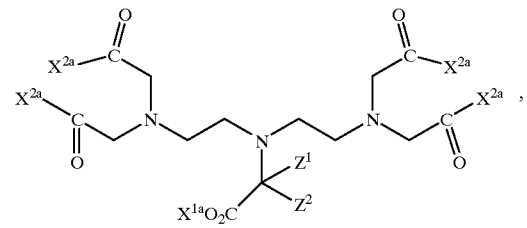

(Ia)

in which
$X^{1a}$ stands for a straight-chain or branched $C_1$–$C_4$ alkyl group or a benzyl group, preferably a tert-butyl, ethyl, isopropyl or a—optionally substituted—benzyl group and
$X^{2a}$ in each case independently of one another, stand for a group O—$X^{1a}$ with $X^{1a}$ in the above-mentioned meaning or $N(R^1)R^2$ with $R^1$ and $R^2$ in the above-mentioned meaning.

The cleavage of the protective groups takes place according to the processes known to one skilled in the art, for example, by hydrolysis, hydrogenolysis, alkaline saponification of the esters with alkali in aqueous or aqueous-alcoholic solution at temperatures of 0° to 80° C., acid saponification with mineral acids or in the case of $^{tert}$-butyl esters with the help of trifluoroacetic acid.

The invention therefore also relates to the process for the production of complexes and complexing agents according to the invention.

Pharmaceutical Agents

Another object of the invention are agents, which contain at least one of the compounds according to the invention as well as a process for the production of these agents, which is characterized in that the complex salt dissolved in water is put into a form suitable for enteral or parenteral administration with the additives and stabilizers usual in galenicals, so that the complex salt is present in a concentration of 1 to 1500 mmol/l preferably in a concentration of 10 to 1000 mmol/l. The resulting agents are then optionally sterilized. They are administered generally in a dose of 1 to 300 ml on the basis of the diagnostic problem.

Suitable additives are, for example, physiologically harmless buffers (such as, e.g., tromethamine), small additions of complexing agents (such as, e.g., diethylenetriaminepentaacetic acid) or, if necessary, electrolytes, such as, e.g., sodium chloride or, if necessary, antioxidants, such as, e.g., ascorbic acid.

If suspensions or solutions of the agents according to the invention in water or physiological salt solution are desired for enteral administration or other purposes, they are mixed with one or more adjuvants usual in galenicals (e.g., methylcellulose, lactose, mannitol), and/or surfactants (e.g., lecithins, Tweens®), Myrj®) and/or flavoring substances for taste correction (e.g., ethereal oils).

In principle, it is also possible to produce the diagnostic agents according to the invention even without isolating the complex salts. In each case, special care must be used to undertake the chelation, so that the salts and salt solutions according to the invention are practically free of noncomplexed metal ions having a toxic effect.

This can be assured, for example, with the help of color indicators, such as xylenol orange, by control titrations during the production process. The invention therefore also relates to a process for the production of complex compounds and their salts. A purification of the isolated complex salt remains as a final precaution.

The substances according to the invention meet the varied requirements which are to be imposed for contrast media in modern diagnosis. The compounds and agents produced from them are distinguished by a high absorption coefficient for x rays, a relaxivity, a good compatibility, which is necessary to maintain the noninvasive nature of the investigations, a high effectiveness, which is necessary to load the body with the smallest possible amounts of foreign substances, a good water solubility (this allows for the production of highly-concentrated solutions, as they are necessary especially for use as x-ray contrast media. Thus, the volume load of the circulatory system is kept within reasonable limits), a low viscosity, low osmolality, advantageous precipitation kinetics.

Further, the agents according to the invention exhibit not only a high stability in vitro, but also a surprisingly high stability in vivo, so that a release or an exchange of ions—toxic in themselves—not covalently bound to the complexes does not take place within the time in which the new contrast media are completely excreted again.

In addition to the high water solubility, which, surprisingly, was able to be increased in the presence of metal ions in a range necessary for diagnostic radiology, the complex compounds according to the invention have a positive effect in diagnostic radiology in that they surprisingly permit investigations with shorter-wave x-ray radiation than that which is possible with conventional contrast media, by which the radiation exposure of the patient is clearly reduced, since, as is generally known, soft radiation of tissue is much more greatly absorbed than hard (R. Felix, Das Röntgenbild [The X-Ray Image]; Thieme Stuttgart 1980).

For use in diagnostic radiology, the complexes of the following metals according to the invention are especially suitable: gadolinium, terbium, dysprosium, holmium, erbium, ytterbium, lutetium, bismuth and hafnium.

Because of the advantageous absorption properties of the contrast media according to the invention in the area of hard x-ray radiation, the agents are also especially suitable for digital subtraction techniques (which work with higher tube voltages).

It is to be emphasized further that the compounds according to the invention are distinguished by an improved heart/circulatory system compatibility in comparison with other complex compounds.

The surprisingly advantageous in vivo distribution behavior of the agents according to the invention is especially to be emphasized. This permits, for the first time, with a low dose for x-ray contrast media (0.1–1 mmol/kg of body weight), the production of x-ray pictures of high diagnostic informative value in the area of the liver, as well as of the bile ducts and the gallbladder.

The pharmaceutical agents according to the invention are generally dosed in amounts of 0.001–20 mmol/kg of body weight. In general, the agents according to the invention for use as diagnostic agents are dosed in amounts of 0.001–5 mmol/kg of body weight, preferably 0.005–0.5 mmol/kg of body weight. Details of the use are discussed for example in H. J. Weinmann, et al., Am. J. of Roentgenology 142, 619 (1984). In general, the agents according to the invention are dosed for use as x-ray contrast media in the amounts of 0.1–20 mmol/kg of body weight, preferably 0.25–5 mmol/kg of body weight. Details of the use of x-ray contrast media are discussed for example, in Barke, Rötgenkontrastmittel [X-ray Contrast Media], G. Thieme, Leipzig (1970) and P. Thurn, E. Bucheler "Einführung in die Rötgendiagnostik [Introduction into X-ray Diagnosis]," G. Thieme, Stuttgart, New York (1977).

In addition to use in diagnostic radiology, the agents according to the invention, which contain in the complex a paramagnetic metal ion of an element of atomic numbers 20–32, 39–51 or 57–83, can also be used in NMR diagnosis. This dual nature opens up further fields of use. Thus, these agents according to the invention are then always to be used advantageously if a combination of x-ray and NMR diagnosis is necessary for differentiated visualization and reliable determination of certain diseases. This is true, e.g., in the case of suspicion of recurrence after tumor operations or radiation therapy. In these cases, the patient is spared an additional load by double administration by use of a contrast medium which is equally suitable for both techniques.

The complexing agents and their complexes according to the invention with weakly bound metals are, moreover, suitable to remove heavy metals from the body, for example, after a heavy metal poisoning. In particular, a detoxification of the liver is possible by the extrarenal excretion of the complexing agents and complexes according to the invention. The use of the compounds according to the invention for the production of agents for reating heavy metal poisonings, especially for treating heavy metal poisonings of the liver, are therefore also the object of the invention.

Further objects of the invention are characterized by the claims.

In general, it has been possible with the mentioned complex compounds to open up new possibilities in diagnostic and therapeutic medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application(s) 195 07 820.9, are hereby incorporated by reference.

EXAMPLES

The following examples are used for a more detailed explanation of the object of the invention without intending to be limited to this object.

Example 1

Dysprosium complex of the disodium salt of N,N-bis-{2-[N',N'-bis-(carboxymethyl)]-amino]-ethyl}-L-3-[(4-ethoxy)-phenyl]-alanine a) N,N-Bis-{2-[N',N'-bis-[(benzyloxycarbonyl)-methyl]-amino]-ethyl}-L-tyrosine benzyl ester 15.5 g (35.0 mmol) of L-tyrosine benzyl ester-4-methylbenzenesulfonate and 33.2 g (79.0 mmol) of N,N-bis-[(benzyloxycarbonyl)-methyl]-2-bromethylamine (M. Williams and H. Rapoport, J. Org. Chem. 58, 1151 (1993)) are introduced in 70 ml of acetonitrile and mixed with 60 ml of 2n phosphate buffer solution (pH 8.0). The batch is vigorously stirred for 24 hours at room temperature, and the aqueous phosphate buffer phase is exchanged after 2 and 8 hours for fresh buffer solution. Then, the organic phase is concentrated by evaporation in a vacuum and the residue is chromatographed on silica gel with hexane/ethyl acetate/triethylamine (3:1:0.01). The product-containing fractions are concentrated by evaporation in a vacuum.

Yield: 23.4 g (70.3% of theory) of colorless oil.

Analysis (relative to the solventless substance): Cld: C 70.79, H 6.26, N 4.42, O 18.52, Fnd: C 70.69, H 6.33, N 4.51 b) N,N-Bis-{2-[N',N'-bis-[(benzyloxycarbonyl)-methyl]-amino]-ethyl}-L-3-[(4-ethoxy)-phenyl]-alanine benzyl ester 20.3 g (21.4 mmol) of the compound produced according to Example 1a) is dissolved in 50 ml of anhydrous N,N-dimethylformamide and mixed at 0° C. under argon with 0.94 g (23.5 mmol) of sodium hydride dispersion (60% in mineral oil). The batch is allowed to stir for 15 minutes, then 3.74 g (24.0 mmol) of ethyl iodide is added, the reaction temperature is allowed to increase to room temperature and it is stirred for another 5 hours. For working-up, the batch is taken up in toluene and shaken out several times from aqueous sodium bicarbonate solution. The organic phase is separated, dried on magnesium sulfate, filtered and concentrated by evaporation. The oily residue is chromatographed on silica gel with hexane/diethyl ether/triethylamine (30:80:1), the product-containing fractions are combined and concentrated by evaporation.

Yield: 18.8 g (89.8% of theory) of colorless oil

Analysis (relative to the solventless substance): Cld: C 71.22, H 6.49, N 4.30, O 17.99, Fnd: C 71.23, H 6.48, N 4.37 c) N,N-Bis-{2-[N',N'-bis-(carboxymethyl)]-amino]-ethyl}-L-3-[(4-ethoxy)-phenyl]-alanine 16.8 g (17.2 mmol) of the decaester described in Example 1b) is dissolved in 145 ml of methanol, mixed with 68.8 ml of 2 n sodium hydroxide solution and stirred for about 5 hours at 60° C. Then, the solution is adjusted to pH 1 with concentrated hydrochloric acid and concentrated by evaporation; the residue is added with strongly acidic ion exchanger on a column and eluted with aqueous ammonia solution. The eluate fractions containing the product are concentrated by evaporation in a vacuum and dried on an oil pump vacuum.

Yield: 9.01 g (99.4% of theory)

Analysis (relative to the solventless substance): Cld: C 52.37, H 6.31, N 7.97, O 33.36, Fnd: C 52.21, H 6.32, N 7.87 d) Dysprosium complex of the disodium salt of N,N-bis-{2-[N',N'-bis-(carboxymethyl)]-amino]-ethyl}-L-3-[(4-ethoxy)-phenyl]-alanine 8.45 g (16.02 mmol) of the deca acid described in Example 1c) is taken up in 25 ml of water, mixed with 2.57 g (7.10 mmol) of dysprosium oxide and stirred for 3 hours at 60° C. Then, it is adjusted with diluted sodium hydroxide solution to pH 7.2, filtered, and the filtrate is freeze-dried.

Yield: 11.54 g (98.6% of theory) of colorless lyophilizate

Analysis (relative to the anhydrous substance): Cld: C 37.79, H 3.86, Dy 20.89, N 5.58, Na 6.11, O 23.38, Fnd: C 37.88, H 3.91, Dy 20.80, N 5.62, Na 6.18

The following complexes are produced analogously:

a) Bismuth complex of the disodium salt of N,N-bis-{2-[N',N'-bis-(carboxymethyl)]-amino]-ethyl}-L-3-[(4-ethoxy)-phenyl]-alanine Analysis (relative to the anhydrous substance): Cld: C 35.53, H 3.63, Bi 26.88, N 5.41, Na 5.91, O 22.64, Fnd: C 35.24, H 3.82, Bi 26.76, N 5.33, Na 5.63 b) Manganese complex of the trisodium salt of N,N-bis-{2-[N',N'-bis-(carboxymethyl)]-amino]-ethyl}-L-3-[(4-ethoxy)-phenyl]-alanine Analysis (relative to the anhydrous substance): Cld: C 42.74, H 4.37, Mn 8.50, N 6.50, Na 10.67, O 27.23, Fnd: C 42.58, H 4.51, Mn 8.36, N 6.47, Na 10.54 c) lutetium complex of the N,N-bis-(2-[N',N'-bis-(carboxymethyl)-amino]-ethyl)-L-3-[(4-ethoxy)-phenyl]-alanine Analysis (relative to the anhydrous substance): Cld: C 37.16, H 3.80, N 5.65, O 23.67, Lu 23.53, Na 6.18, Fnd: C 37.22, H 3.91, N 5.71, Lu 23.40, Na 6.25

Example 2

Gadolinium complex of the disodium salt of N,N-bis-[2-[N',N'-bis-(carboxymethyl)-amino]-ethyl]-α-aminolauric acid a) α-Aminolauric acid isopropyl ester 50 ml of isopropanol is stirred at 0° C. under argon and mixed drop by drop with 3.12 ml (41.6 mmol) of thionyl chloride. 30 minutes later, 7.40 g (34.4 mmol) of α-aminolauric acid is added in portions, stirred for one hour at room temperature and the batch then is allowed to reflux for two hours. After cooling off to room temperature, the batch is completely concentrated by evaporation, the residue is taken up in tert-butyl methyl ether and shaken out from aqueous sodium carbonate solution. The organic phase is dried on magnesium sulfate, filtered and concentrated by evaporation.

Yield: 7.49 g (92.1% of theory) of colorless oil.

Analysis: Cld: C 69.09, H 12.01, N 5.75, O 13.15, Fnd: C 69.02, H 12.22, N 5.81 b) N,N-Bis-[2-[N',N'-bis-[(tert-butyloxycarbonyl)-methyl)-amino]-ethyl]-α-aminolauric acid isopropyl ester 7.95 g (32.7 mmol) of the amine produced according to Example 2a) and 25.4 g (72.0 mmol) of N,N-bis-[(tert-butyloxycarbonyl)-methyl]-2-bromethylamine (M. Williams and H. Rapoport, J. Org. Chem. 58, 1151 (1993)) are introduced in 50 ml of acetonitrile and mixed with 20 ml of 2n phosphate buffer solution (pH 8.0). The batch is vigorously stirred at room temperature for 24 hours, and the aqueous phosphate buffer phase is exchanged after 2 and 8 hours for fresh buffer solution. Then, the organic phase is concentrated by evaporation in a vacuum and the residue is chromatographed on silica gel with hexane/ethyl acetate/triethylamine (3:1:0.01). The product-containing fractions are concentrated by evaporation in a vacuum.

Yield: 16.0 g (62.3% of theory) of yellowish oil.

Analysis (relative to the solventless substance): Cld: C 64.17, H 10.13, N 5.35, O 20.35, Fnd: C 64.20, H 10.24, N 5.43 c) N,N-Bis-[2-[N',N'-bis-(carboxymethyl)-amino]-ethyl]-α-aminolauric acid 15.3 g (19.5 mmol) of the tert-butyl ester described in Example 2b) is dissolved in 70 ml of methanol, mixed with 77.9 ml of 2n sodium hydroxide solution and stirred for about 5 hours at 60° C. Then, the solution is adjusted with concentrated hydrochloric acid to pH 1 and concentrated by evaporation; the residue is added with strongly acidic ion exchanger on a column and eluted with aqueous ammonia solution. The eluate fractions containing the product are concentrated by evaporation in a vacuum and dried on an oil pump vacuum.

Yield: 9.01 g (86.8% of theory) of light beige solid

Analysis (relative to the anhydrous substance): Cld: C 54.02, H 8.12, N 7.88, O 29.98, Fnd: C 54.11, H 8.05, N 7.79 d) Gadolinium complex of the disodium salt of N,N-bis-[2-[N',N'-bis-(carboxymethyl)-amino]-ethyl]-α-aminolauric acid A suspension of 8.43 g (15.7 mmol) of the penta acid, produced according to Example 2c), in 100 ml of water is mixed with 2.86 g (7.90 mmol) of gadolinium oxide and stirred at 80° C. for 2 hours. Then, 31.6 ml of in sodium hydroxide solution is added with a microburette and stirred for 1 more hour. Then, the solution is stirred at 80° C. after the addition of 0.5 g of activated carbon for 2 hours and filtered. After freeze-drying, the filtrate yields a colorless solid.

Yield: 10.73 g (92.8% of theory)

Analysis (relative to the anhydrous substance): Cld: C 39.39, H 5.23, N 5.74, O 19.81, Gd 21.49, Na 6.28, Fnd: C 39.44, H 5.11, N 5.80, Gd 21.39, Na 6.30

Example 3

Ytterbium complex of the disodium salt of $N_\alpha,N_\alpha$-bis-[2-[N',N'-bis-(carboxymethyl)-amino]-ethyl]-$N_\varepsilon$-benzoyl-L-lysine a) $N_\varepsilon$-Carboxybenzyl-L-lysine isopropyl ester, hydrochloride 28.0 g (100 mmol) of $N_\varepsilon$-carboxybenzyl-L-lysine is introduced in a solution of 13.0 g (110 mmol) of thionyl chloride in 150 ml of isopropanol, stirred at 0° C. Then, stirring is allowed to continue for one hour at room temperature and then refluxing takes place for one hour. With cooling off, a colorless precipitate precipitates, which is suctioned off and is dried in a vacuum.

Yield: 33.1 g (92.3% of theory)

Analysis: Cld: C 56.90, H 7.58, N 7.81, O 17.83, Cl 9.88, Fnd: C 56.83, H 7.44, N 7.77, Cl 10.02 b) $N_\alpha,N_\alpha$-Bis-[2-[N',N'-bis-[(tert-butyloxycarbonyl)-methyl]-amino]-ethyl]-$N_\varepsilon$-carboxybenzyl-L-lysine isopropyl ester 11.73 g (32.7 mmol) of the hydrochloride produced according to Example 3a) and 25.4 g (72.0 mmol) of N,N-bis-[(tert-butyloxycarbonyl)-methyl]-2-bromethylamine (M. Williams and H. Rapoport, J. Org. Chem. 58, 1151 (1993)) is introduced in 50 ml of acetonitrile and mixed with 20 ml of 2 n phosphate buffer solution (pH 8.0). The batch is vigorously stirred at room temperature for 24 hours, and the aqueous phosphate buffer phase is exchanged after 2 and 8 hours for fresh buffer solution. Then, the organic phase is concentrated by evaporation in a vacuum, and the residue is chromatographed on silica gel with hexane/ethyl acetate/triethylamine (3:1:0.01). The product-containing fractions are concentrated by evaporation in a vacuum.

Yield: 18.52 g (65.5% of theory) of yellowish oil.

Analysis (relative to the solventless substance): Cld: C 62.48, H 8.86, N 6.48, O 22.19, Fnd: C 62.37, H 8.75, N 6.53 c) $N_\alpha,N_\alpha$-Bis-[2-[N',N'-bis-[(tert-butyloxycarbonyl)-methyl]-amino]-ethyl]-L-lysine isopropyl ester 18.0 g (20.8 mmol) of the compound described in Example 3b was dissolved in 200 ml of ethanol and, after the addition of 0.9 g of palladium on activated carbon (10% palladium), it was hydrogenated until hydrogen absorption was completed. Then, it was filtered and the filtrate was completely concentrated by evaporation.

Yield: 15.2 g (100% of theory) of yellowish oil

Analysis: Cld: C 60.80, H 9.65, N 7.66, O 21.89, Fnd: C 60.88, H 9.75, N 7.56 d) $N_\alpha,N_\alpha$-Bis-[2-[N',N'-bis-[(tert-butyloxycarbonyl)-methyl]-amino]-ethyl]-$N_\varepsilon$-benzoyl-L-lysine isopropyl ester 15.0 g (20.5 mmol) of the compound prepared according to Example 3c) is dissolved in 50 ml of N,N-dimethylformamide and mixed drop by drop with 3.17 g (22.6 mmol) of benzoyl chloride with stirring at 0° C. Then, it is stirred overnight at room temperature, concentrated by evaporation in a vacuum and the residue is shaken out with dichlcromethane/water. The organic phase is dried on magnesium sulfate, filtered, concentrated by evaporation and the residue is chromatographed on silica gel with dichloromethane/methanol (95:5); after concentration by evaporation, the product-containing fractions yield a colorless oil.

Yield: 14.8 g (86.6% of theory)

Analysis: Cld: C 63.29, H 8.93, N 6.71, O 21.07, Fnd: C 63.18, H 9.02, N 6.66 e) $N_\alpha,N_\alpha$-Bis-[2-[N',N'-bis-(carboxymethyl)-amino]-ethyl]-$N_\varepsilon$-benzoyl-L-lysine A suspension of 14.0 g (16.8 mmol) of the compound produced, according to Example 3d) is dissolved in 100 ml of methanol and mixed with 134 ml of 1 n sodium hydroxide solution. It is stirred for about 5 hours at 60° C. and the penta acid is precipitated by the addition of concentrated hydrochloric acid. The colorless precipitate was suctioned off and dried in a vacuum. The crude product was used without further purification for the subsequent stage.

Yield: 9.55 g (100% of theory)

f) Ytterbium complex of the disodium salt of $N_\alpha,N_\alpha$-bis-[2-[N'N'-bis-(carboxymethyl)-amino]-ethyl]-$N_\varepsilon$-benzoyl-L-lysine 9.00 g (15.8 mmol) of the penta acid prepared according to Example 3e) is mixed in 100 ml of water with 3.12 g (7.91 mmol) of ytterbium oxide and stirred at 100° C. for 2 hours. Then, 31.6 ml of in sodium hydroxide solution is added with a microburette and stirred for 1 more hour. Then, the solution is stirred at 80° C. after the addition of 0.5 g of activated carbon for 2 hours and filtered. After freeze-drying, the filtrate yields a colorless solid.

Yield: 11.26 g (90.9% of theory)

Analysis (relative to the anhydrous substance): Cld: C 38.37, H 3.99, N 7.16, O 22.49, Yb 22.11, Na 5.88, Fnd: C 38.44, H 3.87, N 7.20, Yb 22.07, Na 5.91

Example 4

Terbium complex of the monosodium salt of N,N-Bis-{2-[N'-(carboxymethyl)]-N'-[(benzylcarbamoyl)-methyl]-amino]-ethyl}-L-glutamic acid a) N,N-Bis-{2-[N'',N''-bis-((benzyloxycarbonyl)-methyl)-amino]-ethyl}-L-glutamic acid diethyl ester 17.8 g (74.2 mmol) of L-glutamic acid diethyl ester-produced compound and 70.2 g (167 mmol) of N,N-bis-[(benzyloxycarbonyl)-methyl]-2-bromethylamine (M. Williams and H. Rapoport, J. Org. Chem. 58, 1151 (1993)) is introduced in 70 ml of acetonitrile and mixed with 60 ml of 2 n phosphate buffer solution (pH 8.0). The batch is vigorously stirred at room temperature for 24 hours, and the aqueous phosphate buffer phase is exchanged after 2 and 8 hours for fresh buffer solution. Then, the organic phase is concentrated by evaporation in a vacuum and the residue is chromatographed on silica gel with hexane/ethyl acetate/triethylamine (3:1:0.01). The product-containing fractions are concentrated by evaporation in a vacuum.

Yield: 46.0 g (70.3% of theory) of colorless oil.

Analysis (relative to the solventless substance): Cld: C 66.73, H 6.74, N 4.76, O 21.77, Fnd: C 66.69, H 6.75, N 4.81 b) N,N-Bis-{2-[N'',N''-bis-(carboxymethyl)-amino]-ethyl}-L-glutamic acid diethyl ester 45.5 g (51.6 mmol) of the compound produced according to Example 4a) is dissolved in 250 ml of ethanol after the addition of 2.5 g of palladium on activated carbon (10% Pd) and hydrogenated under hydrogen atmosphere until hydrogen absorption has been completed. After filtration and concentration by evaporation of the filtrate in a vacuum, a colorless solid is obtained.

Yield: 26.9 g (100% of theory)

Analysis: Cld: C 48.36, H 6.76, N 8.06, O 36.81, Fnd: C 48.33, H 6.79, N 8.10, O 36.70 c) N,N-Bis-[2-(2,6-dioxomorpholino)-ethyl]-L-glutamic acid diethyl ester 26.0 g (49.9 mmol) of the compound produced according to Example 4b) is refluxed in 100 ml of acetic anhydride for one hour. Then, it is concentrated by evaporation at normal pressure to a volume of 50 ml and completely concentrated by evaporation in a vacuum. The residue is taken up in toluene, and the solution is again concentrated by evaporation; this process is repeated three times. In the end, the residue is carefully dried on an oil pump vacuum.

Yield: 22.9 g (100% of theory) of colorless oil

Analysis: Cld: C 51.95, H 6.44, N 8.66, O 32.96, Fnd: C 51.81, H 6.60, N 8.77 d) Terbium complex of monosodium salt of N,N-bis-{2-[N'-(carboxymethyl)]-N'-[(benzylcarbamoyl)-methyl]-amino]-ethyl}-L-glutamic acid 22.0 g (45.3 mmol) of the compound produced according to Example 4c) is dissolved in 50 ml of tetrahydrofuran, and after the addition of 9.71 g (90.6 mmol) of benzylamine, it is stirred at 50° C. until the reaction is completed (determined by thin-layer chromatography). Then, 102 ml of 2 n sodium hydroxide solution is added, stirred for 2 hours at 60° C., adjusted to pH 1 with concentrated hydrochloric acid, greatly concentrated by evaporation on a rotary evaporator and the residue is purified by ion exchange chromatography (cation exchanger (H+form), eluent: aqueous ammonia solution). The eluate is concentrated by evaporation and rigorously dried on a high vacuum, by which the free complex ligand is obtained. The hexa acid is taken up in 250 ml of water and mixed with 8.29 g (22.7 mmol) of terbium oxide. The suspension is stirred for 2 hours at 90° C. and filtered. Then, it is adjusted with in sodium hydroxide solution to pH 7.3. Then, after the addition of 0.5 g of activated carbon, the solution is stirred for 2 hours at 80° C. and filtered. After freeze-drying, the filtrate yields a colorless solid.

Yield: 27.4 g (73.6% of theory)

Analysis (relative to the anhydrous substance): Cld: C 45.32, H 4.54, N 8.52, O 19.47 Tb 19.34, Na 2.80, Fnd: C 45.45, H 4.68, N 8.57 Tb 19.27, Na 2.77

Example 5

Gadolinium complex of the disodium salt of N,N-bis-{2-[N',N'-bis-(carboxymethyl)]-amino]-ethyl}-3-[4-nitrophenyl]-alanine A suspension of 10.57 g (20 mmol) of N,N-bis-{2-[N',N'-bis-(carboxymethyl)]-amino]-ethyl}-3-[4-nitrophenyl)-alanine (M. Williams and H. Rapoport, J. Org. Chem. 58, 1151 (1993)) in 145 ml of water is mixed with 3.62 g (10 mmol) of gadolinium oxide and stirred at 85° C. for five hours. Then, 40.25 ml of in sodium hydroxide solution is added with a microburette and stirred for two more hours. Then, after the addition of 0.8 g of activated carbon, the solution is stirred at 80° C. for one hour and filtered. After freeze-drying, the filtrate yields a colorless solid.

Yield: 13.65 g (93.9% of theory)

Analysis (relative to the anhydrous substance): Cld: C 34.71, H 3.19, N 7.71, O 26.42, Gd 21.64, Na 6.33, Fnd: C 34.56, H 3.28, N 7.62, Gd 21.49, Na 6.20

Example 6

Ytterbium complex of the trisodium salt of N,N-bis-{2-[N',N'-bis-(carboxymethyl)]-amino]-ethyl}-3-[4-(carboxypropionylamino)-phenyl]-alanine a) N,N-Bis-{2-[N',N'-bis-(carboxymethyl)]-amino]-ethyl}-3-[4-(carboxypropionylamino)-phenyl]-alanine 5.2 g (52 mmol) of succinic anhydride is added at room temperature to a suspension of 24.9 g (50 mmol) of N,N-bis-{2-[N',N'-bis-(carboxymethyl)]-amino]-ethyl}-3-[4-aminophenyl]-alanine (M. Williams and H. Rapoport, J. Org. Chem. 58, 1151 (1993)) in 200 ml of anhydrous dioxane, stirred with exclusion of moisture. The batch is stirred for six hours at room temperature and then concentrated by evaporation. The residue is taken up in ½n sodium hydroxide solution, extracted with ethyl acetate and the acid with concentrated hydrochloric acid at pH 1 precipitates the aqueous phase.

Yield: 25.2 g (84.2% of theory) of colorless solid.

Analysis (relative to the solventless substance): Cld: C 50.17, H 5.72, N 9.36, O 34.75, Fnd: C 50.26, H 5.64, N 9.18 b) Ytterbium complex of the trisodium salt of N,N-bis-{2-[N',N'-bis-(carboxymethyl)]-amino]-ethyl}-3-[4-(carboxypropionylamino)-phenyl]-alanine A suspension of 23.94 g (40 mmol) of N,N-bis-{2-[N',N'-bis-(carboxymethyl)]-amino]-ethyl}-3-[4-(carboxypropionylamino)-phenyl]-alanine in 285 ml of water is mixed with 7.88 g (20 mmol) of ytterbium oxide and stirred at 90° C. for four days. Then, 80.5 ml of 1n sodium hydroxide solution is added with a microburette and stirred for two more hours. Then, after the addition of 1.2 g of activated carbon, the solution is stirred at 80° C. for one hour and filtered. After freeze-drying, the filtrate yields a colorless solid.

Yield: 28.7 g (86% of theory)

Analysis (relative to the anhydrous substance): Cld: C 35.98, H 3.38, N 6.71, O 24.92, Yb 20.74, Na 8.26, Fnd: C 35.75, H 3.44, N 6.58, Yb 20.63, Na 8.01

The following complex is produced analogously:

Hafnium complex of the disodium salt of N,N-bis-{2-[N',N'-bis-(carboxymethyl)]-amino]-ethyl}-3-[4-(carboxypropionylamino)-phenyl]-alanine Analysis (relative to the anhydrous substance): Cld: C 36.75, H 3.45, N 6.86 ) 25.46 Hf 21.85, Na 5.63, Fnd: C 36.66, H 3.61, N 6.70 Hf 21.67, Na 5.35

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of general formula I

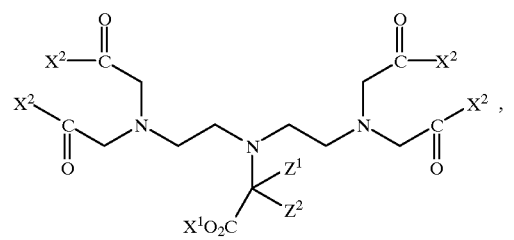

in which
each $X^1$ independently of one another, is a hydrogen atom or a metal ion equivalent of an element of atomic numbers 20–32, 39–51 or 57–83,
each $X^2$ independently of one another, is a group O—$X^1$ wherein $X^1$ has the above-identified meaning,
or N($R^1$)$R^2$ in which
each $R^1$, $R^2$ independently of one another, is
a) a hydrogen atom or b) a saturated or unsaturated, branched or straight-chain $C_1$–$C_{20}$ chain or a cyclic or bicyclic unit formed from a $C_1$–$C_{20}$ chain or part of a $C_1$–$C_{20}$ chain, which
(i) is interrupted by zero to three moieties selected from the group consisting of oxygen atoms, sulfur atoms, sulfoxy groups, sulfono groups, and combinations thereof,
(ii) is substituted by zero to six moieties selected from the group consisting of phenyl, pyridyl, $R^3$S, $R^3$OOC, $R^3$O groups and combinations thereof, and
(iii) further contains zero to three moieties selected from the group consisting of

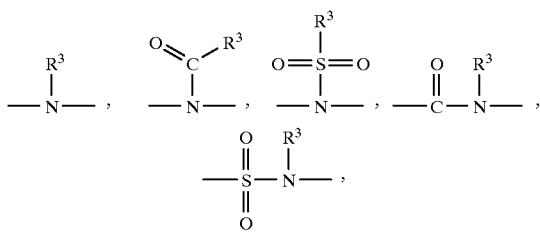

carbonyl groups, thiocarbonyl groups and combinations thereof,
and the phenyl and pyridyl groups are substituted zero to three times, independently of one another, by moieties selected from the group consisting of $R^3O_2C$,

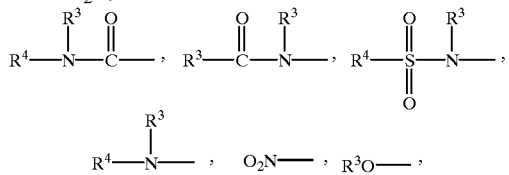

$R^4$ groups and combinations thereof
or $N(R^1)(R^2)$ is a four- to eight-membered ring, which is unsubstituted or substituted by moieties selected from the group consisting of two additional oxygen atoms, two carbonyl groups and combinations thereof, and at least two of the radicals with $X^1$ have $X^1$ as a metal ion equivalent of an element of atomic numbers 20–32, 39–51 and 57–83, $Z^1$ is a saturated or unsaturated, branched or straight-chain $C_6$–$C_{20}$ chain, substituted by 0 to 6 $R^3OOC$ groups $Z^2$ is a) a hydrogen atom or b) a saturated or unsaturated, branched or straight-chain $C_1$–$C_{20}$ chain, or a cyclic or bicyclic unit formed by a $C_6$–$C_{20}$ chain or part of a $C_6$–$C_{20}$ chain, which
  (i) is interrupted by zero to three oxygen atoms
  (ii) is substituted by zero to six moieties selected from the group consisting of phenyl,
$R^3OOC$, $R^3O$ groups and combinations thereof
and the phenyl groups are substituted zero to three times, independently of one another, by moieties selected from the group consisting of $R^3O_2C$—, $R^3O$, $R^3$ groups and combinations thereof,
  each $R^3$ independently of one another, is a) a hydrogen atom or b) a phenyl radical or a straight-chain, branched or cyclic $C_1$–$C_6$ radical, which
    (i) is interrupted by zero to two moieties selected from the group consisting of oxygen atoms, phenylene groups and combinations thereof,
    (ii) is substituted with moieties selected from the group consisting of zero to three HO radicals, zero to three HOOC radicals, zero to two phenyl radicals, and combinations thereof,
  each $R^4$ independently of one another, is a phenyl radical or a straight-chain, branched or cyclic $C_1$–$C_6$ radical, which is interrupted by zero to two moieties selected from the group consisting of oxygen atoms, phenylene groups and combinations thereof, and is substituted with moieties selected from the group consisting of zero to three HO radicals, zero to three HOOC radicals, zero to two phenyl radicals and combinations thereof,
in which free carboxylic acid groups not used for complexing of the compounds of general formula I according to the invention are optionally present in the form of their salts with physiologically compatible inorganic cations, organic cations, or both.

2. Compounds according to claim 1, in which all groups referred to with $X^2$ stand for radical O—$X^1$, in which $X^1$ has the meaning mentioned in claim 1.

3. Compounds according to claim 1, in which one or two of the groups referred to with $X^2$ stand for a radical $N(R^1)R^2$, in which $R^1$ and $R^2$ have the meaning mentioned in claim 1.

4. Compounds according to claim 1, in which sodium, calcium, magnesium, zinc, meglumine, glucosamine, arginine, ornithine, lysine and/or ethanolamine ions are present as physiologically compatible cations.

5. Compounds according to claim 1, in which $Z^1$ stands for a $C_6$–$C_{20}$ alkyl radical substituted by 1 to 6, $R^3OOC$ groups.

6. Compounds according to claim 1, in which $Z^1$ stands for a radical of formula —$(CH_2)_n$—COOH, in which n stands for numbers 6 to 19.

7. Metal complexes of the compound according to claim 1, in which as metal, a paramagnetic metal is contained.

8. Metal complexes of the compound according to claim 1, in which the metal is radioactive.

9. Pharmaceutical composition containing at least one physiologically compatible compound according to claim 1, with additives usual in galenicals.

10. A compound according to claim 1 in which $Z^1$ is a —$(CH_2)_9$COOH group.

11. Metal complexes of the compound of claim 1 wherein the metal is selected from the group consisting of metals of the lanthanoid series.

12. Metal complexes of the compound of claim 1 wherein the metal is selected from the group consisting of gadolinium, dysprosium, holmium, erbium, terbium, lutetium and ytterbium.

13. Metal complexes of the compound of claim 1 wherein the metal is selected from the group consisting of bismuth and hafnium.

14. Metal complexes of the compound of claim 1 wherein the metal is selected from the group consisting of manganese and iron.

15. Metal complexes of the compound of claim 1 wherein the metal is selected from the group consisting of gallium, indium and technetium.

16. Metal complexes of the compound of claim 1 wherein the metal is selected from the group consisting of calcium or zinc.

17. A compound of claim 1 wherein $Z^1$, is a $C_9$–$C_{20}$ alkyl chain.

18. A process for the production of compounds of claim 1 comprising
  a) converting a compound of general formula 1a to complexing agents of general formula 1b by cleavage of an acid protective group and
  b) converting the complexing agent to a metal complex by reaction with a metal oxide or metal salt of an element of atomic numbers 20–32–39–51 or 57–83, wherein compounds of general formulae Ia and Ib are (Ia)

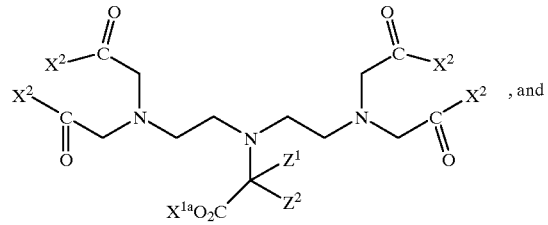

, and

-continued

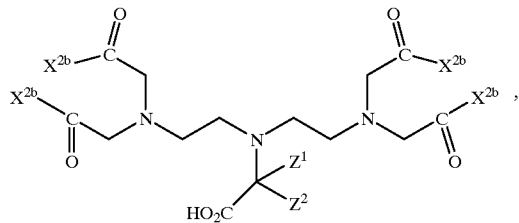

(Ib)

in which $Z^1$ and $Z^2$ have the meaning mentioned in claim 1, each $X^{1a}$, independently of one another, is a $C_1$–$C_4$ alkyl group or an optionally substituted benzy group, each $x^{2a}$ independently of one another, is a group O—$X^{1a}$ wherein $X^{1a}$ has the above identified meaning, or $N(R^1)R^2$ and each $X^{2b}$ is independently of one another a group OH or $N(R^1)R^2$, wherein $R^1$ and $R^2$ are as defined in claim 1.

* * * * *

UNITED STATES PATENT AND TRADEMARK OFFICE
CERTIFICATE OF CORRECTION

PATENT NO.     : 6,254,850 B1
DATED          : July 3, 2001
INVENTOR(S)    : Krause et al.

It is certified that error appears in the above-identified patent and that said Letters Patent is hereby corrected as shown below:

<u>Column 22,</u>
Line 5, change "benzy" to -- benzyl --.

Signed and Sealed this

Twenty-first Day of May, 2002

*Attest:*

*Attesting Officer*

JAMES E. ROGAN
*Director of the United States Patent and Trademark Office*